United States Patent [19]
Haitko et al.

[11] Patent Number: 6,063,952
[45] Date of Patent: May 16, 2000

[54] PROCESS FOR MAKING A TETRAARYLOXYMETHANE USING A CUPRIC ALKOXIDE

[75] Inventors: Deborah Ann Haitko; Marsha Mottel Grade, both of Schenectady, N.Y.

[73] Assignee: General Electric Company, Schenectady, N.Y.

[21] Appl. No.: 09/134,407

[22] Filed: Aug. 14, 1998

[51] Int. Cl.[7] .......................... C07C 68/00; C07C 41/60
[52] U.S. Cl. ...................... 558/274; 558/277; 568/592
[58] Field of Search ...................... 558/274, 277; 568/592

[56] References Cited

U.S. PATENT DOCUMENTS 5,504,238  4/1996  Colburn ................... 558/274
5,663,406  9/1997  King, Jr. et al. ................ 558/243

FOREIGN PATENT DOCUMENTS

720979A1  7/1996  European Pat. Off. .

Primary Examiner—Michael G. Ambrose
Attorney, Agent, or Firm—Noreen C. Johnson; Douglas E. Stoner

[57] ABSTRACT

Carbonate ester is produced by acid hydrolysis of the reaction product of cupric alkoxide induced reaction between a hydroxy compound and a sulfur compound in a melt process. Diaryl carbonate is produce by hydrolysis of the resulting orthoester.

15 Claims, 3 Drawing Sheets

PROCESS FOR MAKING A TETRAARYLOXYMETHANE USING A CUPRIC ALKOXIDE

This invention is directed to manufacture of carbonate esters and more particularly to production of carbonate esters by cupric alkoxide induced reaction of a hydroxy compound with a sulfur compound, optionally, in the presence of a solubilizing ligand to make tetraaryloxyalkane which can be converted to the carbonate ester by acid hydrolysis.

BACKGROUND OF THE INVENTION

Polycarbonate resin, particularly bisphenol A polycarbonate, is an important engineering thermoplastic with many uses in construction, glazing and optical applications. Polycarbonate resin can be made by interfacial reaction or by melt transesterification. The melt transesterification technology has a significant environmental advantage over the interfacial process which uses phosgene for reaction with hydroxy compounds such as bisphenols. In addition melt process materials have lower levels of contaminants which make the very desirable for critical optical applications such as making compact disks.

Strong interest in the melt process technology is in part dependant on development of a satisfactory manufacturing process for the carbonate esters such as diphenyl carbonate.

Numerous methods are employed to synthesize diphenyl carbonate. The two current commercially viable methods to produce diphenyl carbonate are: 1) phosgenation of phenol in an interfacial process and 2) the titanium-catalyzed transesterification of dimethylcarbonate with phenol.

The conversion of carbon disulfide and phenol into tetraphenoxymethane is known. This reaction is effected by the use of a cuprous phenoxide complex, prepared insitu in an organic solvent by reaction of sodium phenoxide with cuprous chloride. Hydrolysis of tetraphenoxymethane to diphenyl carbonate is also known. A melt-based, solventless system in which carbon disulfide, cupric oxide ($Cu_2O$) and phenol are combined and reacted in one step without the need for preforming the reactive copper phenoxide species is also known.

SUMMARY

High yields of tetraphenoxymethane and diphenylcarbonate have been obtained in short reaction times by a copper-induced condensation of phenol and carbon disulfide, when cupric alkoxides, such as cupric methoxide, are employed in the synthesis. The addition of appropriate phosphorus- or amine-containing ligands increases both the initial rate and the total yield.

The development of efficient routes for the preparation of diphenyl carbonate is required to fully exploit the melt-based technology using diphenyl carbonate and bisphenol to prepare polycarbonate resin. Environmental pressures are directing manufacturing away from the traditional phosgene reactions to make intermediates, such as diphenyl carbonate, that can be used in a transesterification process to produce polycarbonate.

We have found that the use of copper(II) alkoxides increase the rate of formation of tetraphenoxymethane and diphenyl carbonate significantly, with up to 80% yield by 1 hr. The addition of small amounts of phosphorus or amine-containing ligands to the copper(II) alkoxide-mediated reactions has the ability to increase the initial rate and final yield even more dramatically, with up to 80% reaction achieved within 5–15 minutes and total yields of 120–130%. Compared to these reactions, the extent of the fundamental, non-ligand containing reactions at 15 minutes is only 2–10%.

The overall reaction is illustrated below for tetraphenoxymethane and diphenyl carbonate.

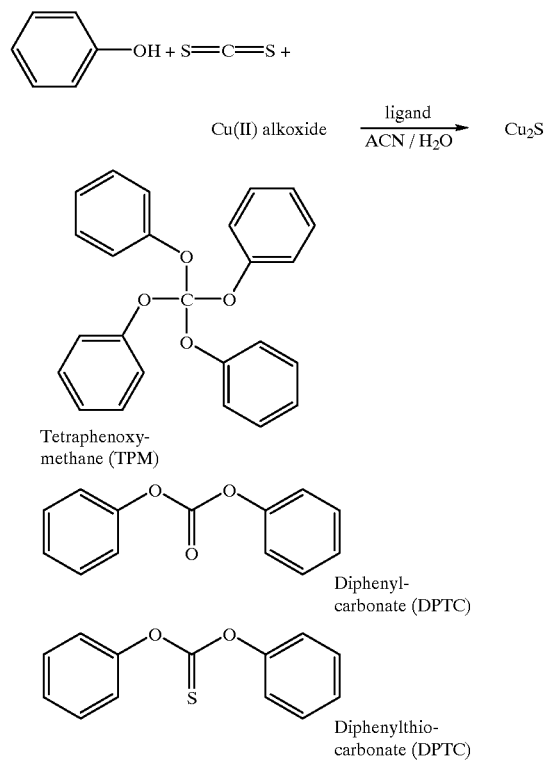

Cu(II) alkoxide = copper(II) methoxide; copper(II) acetate.
ligand = none, triphenylphosphine, triphenylphosphite, 2,2'-dipyridyl amine, tetraethylethylenediamine.

DESCRIPTION OF THE INVENTION

Figure 1:
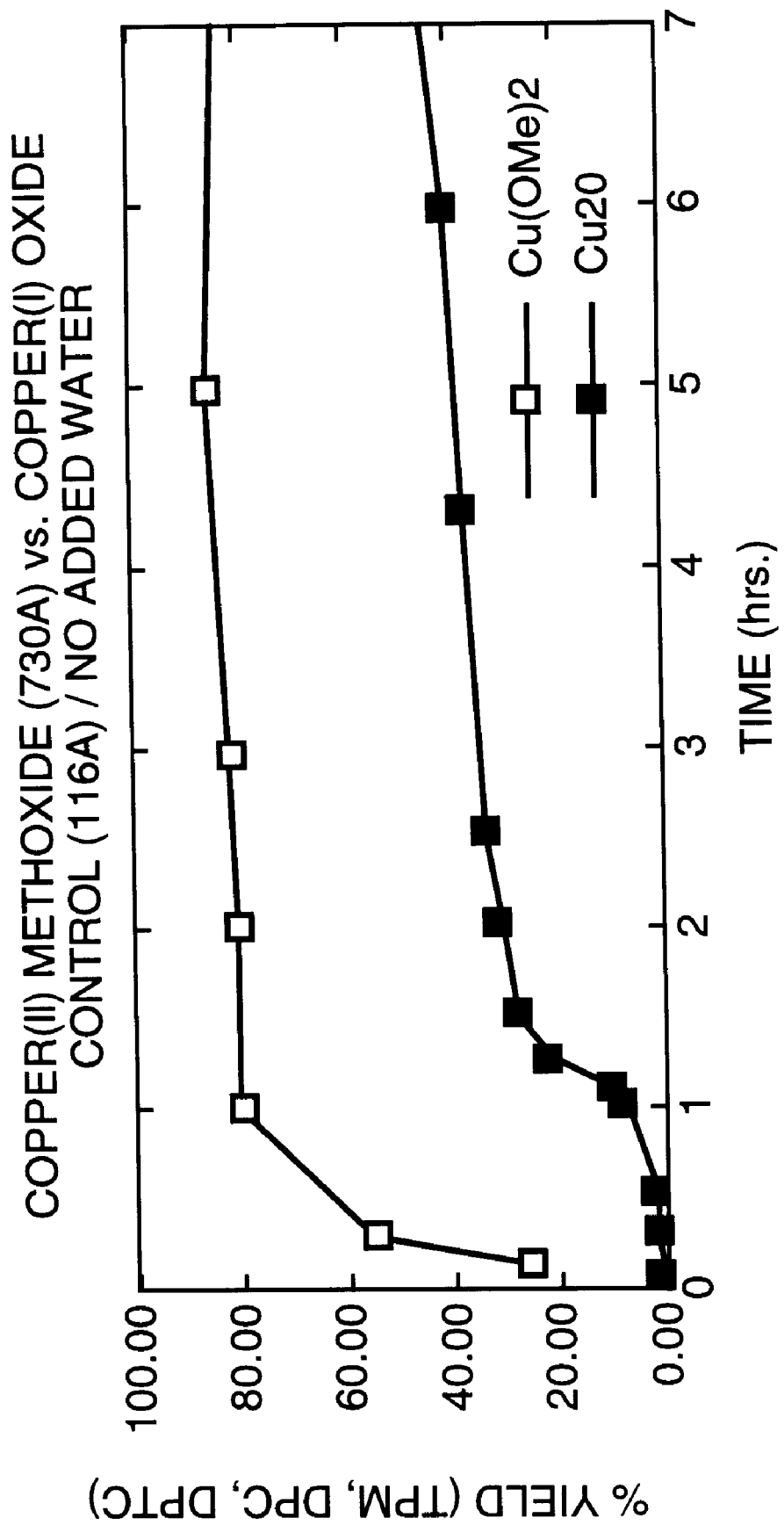
FIG. 1: Comparison of Initial Rates for Reactions using Different Copper Compounds with phenol and $CS_2$ to Form TPM (no added water): Copper(II) Methoxide (730A) and Copper(I) Oxide (116A).
Figure 2:
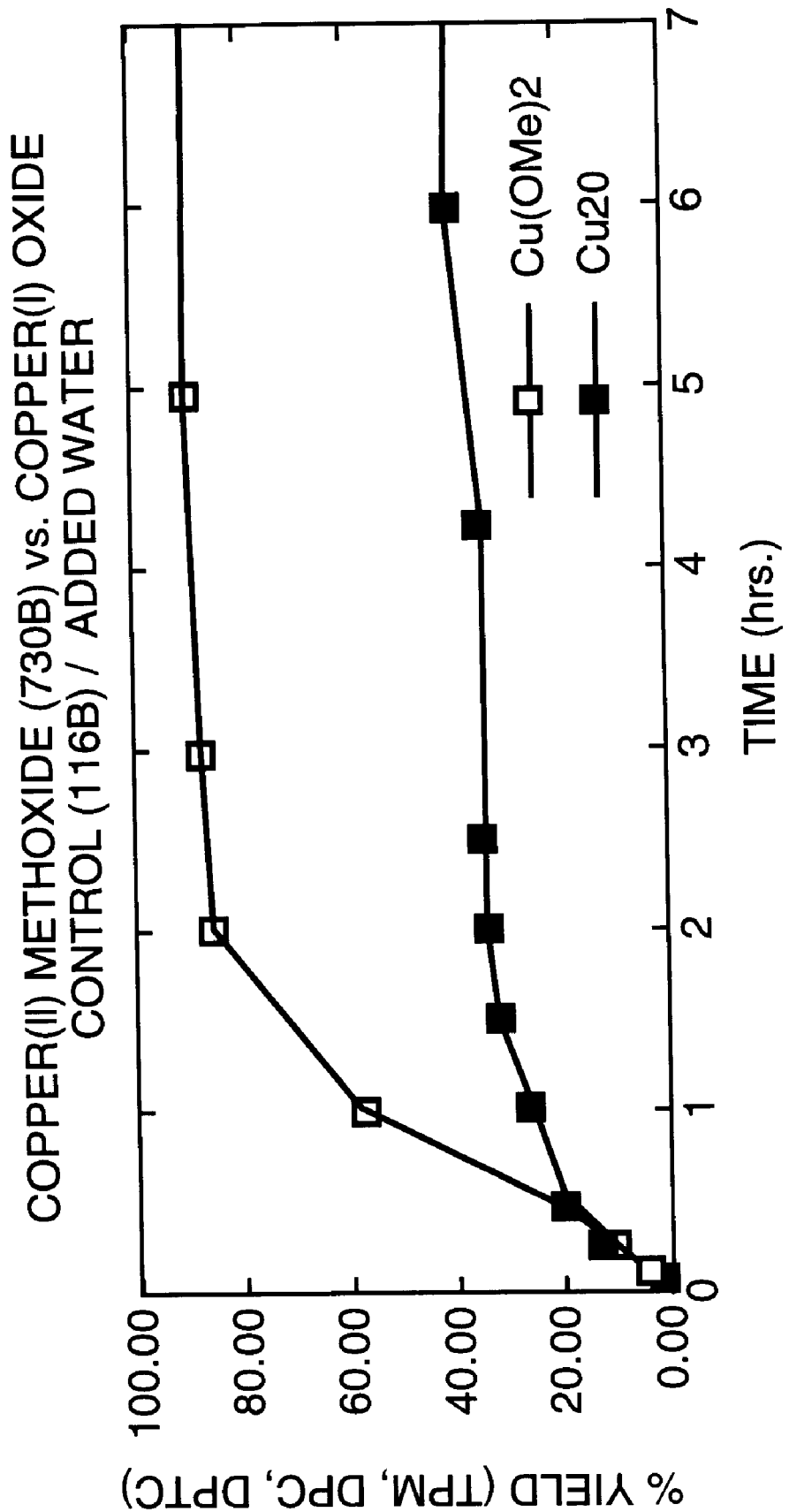
FIG. 2: Comparison of Initial Rates for Reactions using Different Copper Compounds with phenol and $CS_2$ to Form TPM (added water): Copper(II) Methoxide (730B) and Copper(I) Oxide (116B).

Melt reactions using carbon disulfide and phenol in conjunction with copper(II) alkoxides resulted in greatly improved reaction rates and high yields of TPM/DPC. The overall reaction is shown in Scheme 1. Up to 80% yield by 1 hour can be achieved when using copper(II) methoxide (730A). FIG. 1 compares the overall yields for the first 7 hours of an enhanced reaction using copper(II) methoxide (730A) versus a copper(I) oxide-mediated control reaction (116A) when no added water is present. FIG. 2 compares the analogous reactions when a water-phase is added: the copper (II) methoxide-mediated reaction (730B) and a copper(I) oxide-mediated control reaction (116B). All of the reactions were run at 65°C, with stirring, under a nitrogen blanket. The heterogeneous experiments were sampled throughout the 22–30 hr reaction time; the production of products was monitored by GC-FID. The copper(II) alkoxides that were screened were copper(II) methoxide (Cu(OMe)$_2$) and copper(II) acetate (Cu(OAc)$_2$).

The instant invention provides a method of producing carbonate ester comprising the step of admixing and reacting an aliphatic, cycloaliphatic, or aromatic hydroxy compound of the formula

R—OH, wherein R is selected from the group consisting of substituted and unsubstituted alkyl radicals, and substituted and unsubstituted aryl radicals; a sulfur compound selected from the group consisting of the formulas

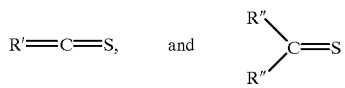

wherein R' is O or S, and R" is OR; and a promoter comprising at least one metal source that is capable of reacting with said hydroxy compound and said sulphur compound.

Enhancement of the reaction rate and yield through the addition of ligands in the copper(II) methoxide system was also tested. These reactions utilized copper(II) methoxide with various ligands, at a 10 mole percent level; the ligands chosen were representative of the types of ligands that had previously been found to increase rate and or yield: triphenylphosphine (TPP), triphenylphosphite, 2,2'-dipyridyl amine (22'-DPA), and tetraethylenediamine (TEED). The data for all of the reactions, along with data for control reactions (Cu$_2$O-based reactions without the addition of ligands), are listed in Table 1.

Figure 3:
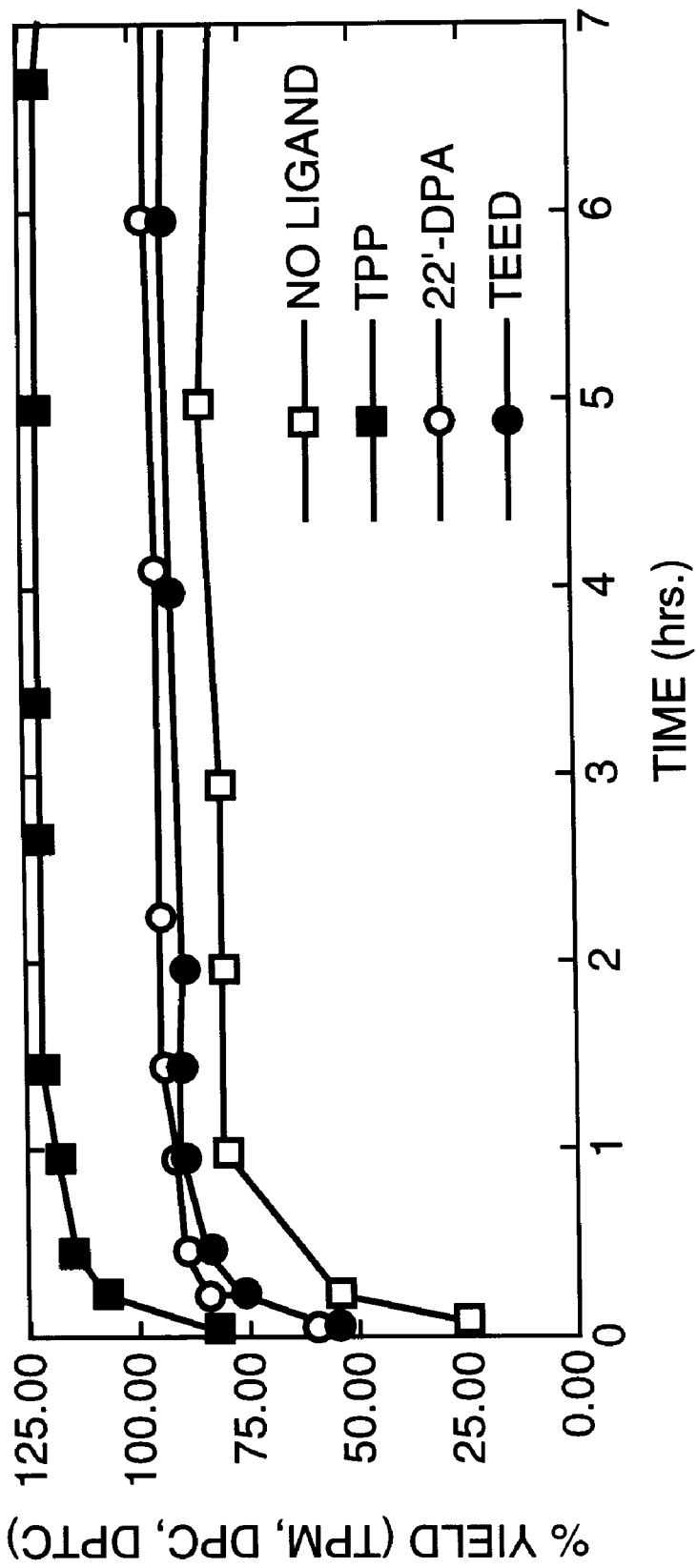
FIG. 3: Comparison of Yields for Reactions using Copper (II) Methoxide with phenol and $CS_2$ to form TPM (no added water) using various ligands

The addition of small amounts, about 0.1 to about 10 mol percent, of phosphorus- or amine-containing ligands to copper(II) methoxide mediated reactions increased the initial rate and final yield even more dramatically than the use of copper(II) methoxide alone; up to 80+% reaction was achieved within 5–15 minutes, with total yields of 115–130% (Table 1: Reactions 88A, 812A, and 826A). All of the ligands used in this study increased the initial rate of the reaction. A comparison of the copper(II) methoxide-mediated reactions with and without the addition of ligand is shown in FIG. 3. In general from about 0.1 to about 10 mol percent of at ligand, based on the copper content of the reaction mixture, provides dramatically improved yields and reaction rates.

TABLE 1

Melt reactions of Cu(II)alkoxides with phenol and carbon disulfide:

Control reactions (using Cu$_2$O), reactions using Cu(II)alkoxides, and reactions with amine and phosphorus-containing ligands

| Reaction # & Catalyst* | Ligand (10 mol %) | ACN? | H$_2$O? | 3 hr yield | Total Yield (22–30 h) | TPM/DPC** |
|---|---|---|---|---|---|---|
| 116A(Cu$_2$O control) | — | Y | N | 34% | 95% (30 h) | 93/2% |
| 116B(Cu$_2$O control) | — | Y | Y | 34% | 78% (30 h) | 21/57% |
| 730A(Cu(OMe)$_2$) | — | Y | N | 80% | 78% (29 h) | 75/3% |
| 730B(Cu(OMe)$_2$) | — | Y | Y | 88% | 94% (29 h) | 34/60% |
| 88A(Cu(OMe)$_2$)*** | TPP | Y | N | 122% | 122% (22 h) | 116/4% |
| 826A(Cu(OMe)$_2$)*** | TPP | Y | Y | 127% | 126% (24 h) | 68/58% |
| 88B(Cu(OMe)$_2$) | TPPhosphite | Y | N | 116% | 110% (22 h) | 108/2% |
| 812A(Cu(OMe)$_2$)*** | 22'-DPA | Y | N | 93% | 94% (22 h) | 81/6% |
| 812B(Cu(OMe)$_2$) | 22'-DPA | Y | Y | 82% | 80% (22 h) | 60/13% |
| 820A(Cu(OMe)$_2$) | TEED | Y | N | 91% | 92% (24 h) | 90/0% |
| 820B(Cu(OMe)$_2$) | TEED | Y | Y | 114% | 91% (24 h) | 81/8% |
| 814A(Cu(OAc)$_2$) | — | Y | N | 48% | 103% (30 h) | 1/102% |
| 814B(CuOAc)$_2$) | — | Y | Y | 0.50% | 34% (30 h) | 0/34% |

*All reactions (except 814B were run at 65° C. under N$_2$, with mechanical stirring,
**remaining amount is DPTC
***These reactions were extremely fast initially; 80+% reaction in 5–15 min.

The level of diphenylthiocarbonate (DPTC; half-product of the reaction), often observed when some of the most active ligands are used at the 10 mole percent level, is lower than in the corresponding Cu$_2$O-mediated system. For example, almost 50% DPTC is produced at the 7 hr point in a Cu$_2$O-mediated reaction when 10 mole percent TPP (131A) is used. Although the DPTC level in this TPP-containing reaction finally decreases to less than about 2% (after 50 hrs), reactions utilizing Cu$_2$O and any of the aromatic amine-containing ligands retain a significant level of DPTC throughout (11–33%). In a similar reaction using copper(II) methoxide with TPP (88A), no more than 2% DPTC is ever noted. Although DPTC should be able to be converted to TPM under favorable conditions, it is beneficial to have the TPM or DPC formed directly, thus precluding unnecessary steps or unneeded reaction times.

The use of copper(II) acetate (Cu(OAc)$_2$), copper (II) propionate, or copper (II) stearate as the copper species increases both the initial rate and final yield slightly in the reaction that contained no water phase (814A). This system may also benefit from the addition of a ligand, as did the copper(II) methoxide system. The copper(II) acetate (Cu(OAc)$_2$) system with added water performed poorly. This may be due to the solubility of $Cu(OAc)_2$ in water that enhances its removal from the organic reactants.

EXPERIMENTAL

The melt reactions were run by combining phenol, copper (II) alkoxide, ligand (if used), internal standards and a small amount of acetonitrile in a round bottom flask; some of the reactions contained water as a second phase. These reagents were stirred for 5 minutes at 45° C. under a nitrogen blanket in order to melt the phenol and disperse the copper(II) alkoxide. The carbon disulfide was added and the temperature was concurrently raised to 65° C., where it was kept for the duration of the reaction. The reaction was carried out at ambient pressure. Representative reactions and their charges are included below. The reagents were used as received with no drying or pre-purification steps.

Copper(II)Methoxide with No Added Ligand ($CH_3CN$, no $H_2O$) (730A)

Into a 250 mL, 3-neck round bottom flask, equipped with an overhead stir paddle, condenser and nitrogen blanket, were placed phenol (29.96 g; 0.318 mol), copper(II) methoxide (2.6405 g; 0.02102 mol), acetonitrile ($CH_3CN$, 2.5 mL; 0.04787 mol), and internal standards [3-methyl anisole (0.3054 g) and biphenyl (0.3010 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.03325 mol) and the temperature of the oil bath was immediately raised to 65° C. for the duration of the reaction (29 h). The stir speed was fast to ensure good mixing of the heterogeneous mixture. During the course of the reaction, a black suspension formed and was dispersed throughout. Samples were taken every 15–30 min. for the first three hours and intermittently thereafter. 0.4 mL samples were pipetted out, diluted with 1.5 mL $CH_3CN$, followed by filtration using Whatman Uniprep filters, containing a 0.45 μm PTFE membrane. Samples were analyzed using a Hewlett Packard 5890 Series II gas chromatograph equipped with a 30 meter DB-1 coated capillary column and a flame ionization detector (FID).

Copper(II)Methoxide with No Added Ligand ($CH_3CN$, $H_2O$) (730B)

Into a 250 mL, 3-neck round bottom flask, equipped with an overhead stir paddle, condenser and nitrogen blanket, were placed phenol (30.05 g; 0.319 mol), copper(II) methoxide (2.6438 g; 0.02105 mol), acetonitrile ($CH_3CN$, 2.5 mL; 0.04787 mol), water (36 mL; 2.0 mol), and internal standards [3-methyl anisole (0.3049 g) and biphenyl (0.2990 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.03325 mol) and the temperature of the oil bath was immediately raised to 65° C. for the duration of the reaction (29 h). The stir speed was fast to ensure good mixing of the heterogeneous mixture. During the course of the reaction, a black suspension formed and was dispersed throughout the emulsion. Samples (0.7 mL) were taken, diluted, filtered and analyzed as stated above.

Copper(II)Methoxide with 10 mol % Triphenylphosphine (TPP) as Added Ligand ($CH_3CN$, no $H_2O$) (88A)

Into a 250 mL, 3-neck round bottom flask, equipped with an overhead stir paddle, condenser and nitrogen blanket, were placed phenol (30.00 g; 0.319 mol), copper(II) methoxide (2.6402 g; 0.02102 mol), triphenylphosphine (TPP; 0.567 g; 0.002162 mol), acetonitrile ($CH_3CN$, 2.5 mL; 0.04787 mol), and internal standards [3-methyl anisole (0.3039 g) and biphenyl (0.2990 g)]. The flask was lowered into a 45° C. oil bath and stirring was commenced. The reaction was mixed, while the phenol melted, for 5 minutes prior to the addition of the carbon disulfide. The carbon disulfide was added (2 mL; 0.03325 mol) and the temperature of the oil bath was immediately raised to 65° C. for the duration of the reaction (29 h). The stir speed was fast to ensure good mixing of the heterogeneous mixture. During the course of the reaction, a black suspension formed and was dispersed throughout. Samples (0.4 mL) were taken, diluted, filtered and analyzed as stated above.

Copper(II)Methoxide with 10 mol % Tetraethyl Ethylenediamine (TEED) as Added Ligand ($CH_3CN$, $H_2O$) (820B)

Into a 250 mL, 3-neck round bottom flask, equipped with an overhead stir paddle, condenser and nitrogen blanket, were placed phenol (34.25 g; 0.364 mol), copper(II) methoxide (2.6464 g; 0.02107 mol), Tetraethyl ethylenediamine (TEED; 0.362 g; 0.003115 mol), water (36 mL; 2.0 mol), acetonitrile ($CH_3CN$, 2.5 mL; 0.04787 mol), and internal standards [3-methyl anisole (0.3039 g) and biphenyl (0.2990 g)]. The flask was lowered into a 45° C. oil bath and stirring was commenced. The reaction was mixed, while the phenol melted, for 5 minutes prior to the addition of the carbon disulfide. The carbon disulfide was added (2 mL; 0.03325 mol) and the temperature of the oil bath was immediately raised to 65° C. for the duration of the reaction (29 h). The stir speed was fast to ensure good mixing of the heterogeneous mixture. During the course of the reaction, a black suspension formed and was dispersed throughout. Samples (0.7 mL) were taken, diluted, filtered and analyzed as stated above.

Copper(II)acetate with No Added Ligand ($CH_3CN$, no $H_2O$) (814A)

Into a 250 mL, 3-neck round bottom flask, equipped with an overhead stir paddle, condenser and nitrogen blanket, were placed phenol (33.44 g; 0.319 mol), copper(II) acetate (2.6386 g; 0.01453 mol), acetonitrile ($CH_3CN$, 2.5 mL; 0.04787 mol), and internal standards [3-methyl anisole (0.3039 g) and biphenyl (0.2990 g)]. The flask was lowered into a 45° C. oil bath and stirring was commenced. The reaction was mixed, while the phenol melted, for 5 minutes prior to the addition of the carbon disulfide. The carbon disulfide was added (2 mL; 0.03325 mol) and the temperature of the oil bath was immediately raised to 65° C. for the duration of the reaction (29 h). The stir speed was fast to ensure good mixing. The reaction was homogeneous and blue-green initially. During the course of the reaction, a black suspension formed and was dispersed throughout; during this time, the reaction slowly turned orange. Samples (0.4 mL) were taken, diluted, filtered and analyzed as stated above.

What is claimed:

1. A process for making carbonate ester comprising preparing and reacting a mixture comprising:
    a hydroxy compound of the formula ROH, in which R is a substituted or unsubstituted aryl radical or a substituted or unsubstituted alkyl radical;
    a sulfur compound selected from the group consisting of the formulas

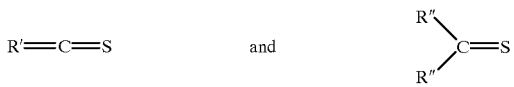

wherein R' is O or S, and R" is OR and
    a cupric alkoxide.

2. The process according to claim 1, which further comprises mixing with the mixture a ligand selected from a monodentate amine and a polydentate amine.

3. The process according to claim 1 wherein the hydroxy compound comprises phenol, cresol, bisphenol A, xylenol, p-cumyl phenyl, n-alkylated phenol or a halogenated phenol.

4. The process according to claim 1 wherein the hydroxy compound is a substituted or unsubstituted phenol.

5. The process according to claim 1 further comprising the step of mixing water with the mixture.

6. The process according to claim 1 wherein the hydroxy compound is phenol, the sulfur compound is carbon disulfide, the cupric alkoxide is cupric methoxide, and the mixture further comprises water and a ligand.

7. The process according to claim 1, further comprising the step of acid hydrolysis of tetraaryloxy methane to carbonate ester.

8. The process according to claim 1 wherein the reaction temperature is in a range between about 40° C. and about 100° C.

9. The process according to claim 1 wherein the reaction is carried out at ambient pressure.

10. The process according to claim 2 wherein the ligand is in a range between about 0.1 mol and about 10 mol percent proportional to the moles of copper in the mixture.

11. The process according to claim 1 wherein the mixture further contains water or dipolar aprotic auxiliary solvent.

12. The process according to claim 7 wherein the tetraaryloxymethane is tetraphenoxymethane.

13. The process according to claim 1 wherein the cupric alkoxide is cupric methoxide.

14. The process according to claim 8 wherein the reaction temperature is about 65° C.

15. The process according to claim 2 wherein the ligand is selected from the group consisting of triphenylphosphine, triphenylphosphite, 2,2'-dipyridyl amine, and tetraethylenediamine.

* * * * *